United States Patent [19]
Jessel et al.

[11] Patent Number: 5,086,642
[45] Date of Patent: Feb. 11, 1992

[54] TEST VESSEL DEVICE FOR TESTING AN APPARATUS FOR MEASURING OR DETECTING A GAS

[75] Inventors: Wolfgang Jessel, Reinfeld; Kurt Masurat, Hamburg, both of Fed. Rep. of Germany

[73] Assignee: Drägerwerk Aktiengesellschaft, Lübeck, Fed. Rep. of Germany

[21] Appl. No.: 452,415

[22] Filed: Dec. 19, 1989

[30] Foreign Application Priority Data

Dec. 24, 1988 [DE] Fed. Rep. of Germany ....... 3843920

[51] Int. Cl.$^5$ ............................................. G01D 18/00
[52] U.S. Cl. ...................................................... 73/1 G
[58] Field of Search .................... 73/23.41, 23.42, 1 G; 436/8, 9

[56] References Cited

U.S. PATENT DOCUMENTS 3,533,272 10/1970 Dahms ................................. 73/1 G
4,998,431 3/1991 Jappinen et al. ..................... 73/1 G

OTHER PUBLICATIONS

Drägerheft 303 (1976) "Neues Messverfahren zur Bestimmung von Schwefelwasserstoffen", G. Wolff, p. 15.

Primary Examiner—Jerry W. Myracle
Attorney, Agent, or Firm—Walter Ottesen

[57] ABSTRACT

The invention is directed to a test vessel device for testing gas measuring and gas detection apparatus wherein a test substance atmosphere of a specific concentration of the test substance is present. The sensor head of a gas measuring apparatus can be introduced into the test vessel device. The test vessel device is improved in that a test substance atmosphere can be provided therein in a state of readiness over a longer time duration and the test substance atmosphere changes only insignificantly with respect to its composition and must not be first produced before carrying out the test. It is intended that the test vessel device be easily producible, have a low weight, be easily manipulable and be convenient to transport as well as be capable of storage. For this purpose, a liquid is introduced into the test vessel device which is closed in a gastight manner with a seal which can be penetrated. The liquid is composed of a solution of the test substance in a solvent inert for the sensor head and in such a quantity and concentration that a vapor is present which is saturated with the test substance.

16 Claims, 1 Drawing Sheet

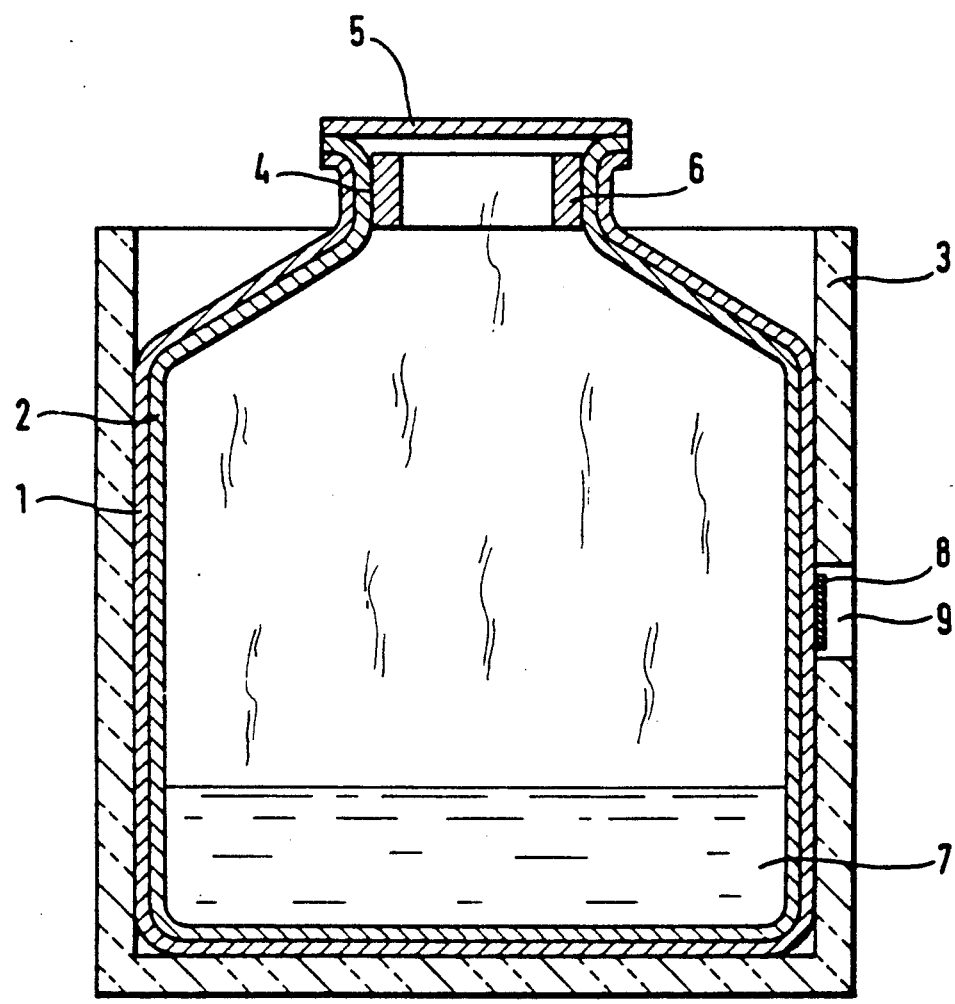

TEST VESSEL DEVICE FOR TESTING AN APPARATUS FOR MEASURING OR DETECTING A GAS

FIELD OF THE INVENTION

The invention relates to a test vessel device for testing gas measuring apparatus and gas detection apparatus wherein an atmosphere of the test substance atmosphere of a specific concentration of a test substance is present. The sensor head of the gas measuring apparatus can be introduced into the test substance atmosphere.

BACKGROUND OF THE INVENTION

A test vessel device of the kind referred to above is described in the German technical journal "Drägerheft", Volume 303, page 15 (1976). The known test vessel device is used for calibrating gas measuring devices such as devices for determining hydrogen sulphide. Test-gas ampules are introduced into a flask for generating a test substance atmosphere. The ampules are mechanically destroyed before use of the test vessel device so that the content of the ampules can distribute in the flask volume. The sensor head of the test apparatus to be calibrated is introduced through an opening into the test vessel and it is intended that the corresponding concentration of hydrogen sulphide will be indicated by the calibrated device.

The known test vessel device has the disadvantage that the test ampules must be produced in advance with the greatest care, that is, the test gas must be mixed and filled into the ampules. The test gas in the ampules can deposit on the glass inner wall surface and thereby falsify the concentration of the test gas. Furthermore, it is inconvenient that the glass ampules must be first broken in the vessel after the sensor head has been introduced. The non-closable opening of the test vessel leads to a mixing of the test atmosphere of the vessel with the ambient air in the event that a long time duration elapses until the sensor head is introduced into the vessel. Furthermore, an intimate mixing of vapors which are heavier than air with the air disposed in the vessel is not assured in each instance. Accordingly, the condition cannot be prevented that the sensor head can be introduced into a region of the vessel wherein the desired test atmosphere is not yet present or thoroughly mixed.

SUMMARY OF THE INVENTION

It is an object of the invention to improve a test vessel device of the kind described above so that a test substance atmosphere is present therein which can be in operational readiness even after a long time duration. It is a further object of the invention to improve the test vessel device in that the test substance atmosphere changes only insignificantly with respect to its composition and must not be produced before carrying out a test. It is intended that the vessel devices be easily produced and be of low weight as well as be convenient to manipulate and comfortable to transport. In addition, the vessels are intended to be capable of storage.

The test vessel device of the invention is for testing an apparatus for measuring or detecting a gas. The apparatus has a sensing head and the test vessel device includes: a vessel having an interior and having an upper portion defining an opening through which the sensing head can be introduced; a liquid disposed in the interior, the liquid being a solution composed of a solvent inert with respect to the sensing head and a test substance of a quantity and concentration so as to cause a vapor to be present in the interior which is saturated with the test substance; and, a penetrable seal for closing off the interior with respect to the ambient in a gastight manner.

The advantage of the invention is seen essentially in that, by means of a defined preparation of the solution, the test substance can be present within the vessel in such a quantity that a stable vapor can form which is saturated with the test substance. Adequate liquid remains even when there is a possible condensation of this vapor on the vessel walls so that the condensation losses can be compensated. The production of a solution mixture is simpler than the production of a defined gaseous test substance having a predetermined concentration.

A liquid quantity of 10 to 20 mL is usually sufficient for a typical vessel volume of approximately 100 mL. The sealed test vessel can be stored with its liquid test substance over a longer period of time. A control can be made in a simple manner to determine if there is still adequate liquid in the test vessel before carrying out the test. The test vessel only has to be shaken. In this way, those test vessels can be separated out wherein the necessary test substance atmosphere can no longer be reliably determined. On the one hand, the test substance can be a substance in solution which is to be detected by the sensor head such as dissolved toluene for a sensor head for determining toluene in air; and, on the other hand, the test substance can also be an alcohol water solution wherein the alcohol of a specific concentration is present. The substance in solution and the alcohol water solution can define a lower explosion limit for detection devices of combustible gas mixtures with the selected percent value being in vapor form. In the first case, a simple test vessel is provided by means of which a calibration of a gas measuring device can be carried out within certain limits. In the second case, concentrations of percentage lower explosion gas limits are available having one and the same test substance mixture with the concentrations being convenient and simple to produce.

The seal is best configured so that it can be broken through by the sensor head in that the seal is pushed through at the periphery of the sensor head by means of a pin or knurled sensor head edge. The remaining edge region of the penetrated seal which remains acts at the same time as a shield for the vapor atmosphere in the vessel with respect to the ambient air.

It is advantageous to provide a receptacle for introducing the sensor head in a vapor-tight manner in the perforated seal in order to further suppress an exchange of the vapor atmosphere with the ambient. This can be achieved, for example, in that the edge of the vessel opening is advantageously narrow and lined with a sealing cover so that the contours of the sensing head can be accommodated thereby.

The formation of a concentration of the test substance present in the saturated vapor atmosphere is also dependent upon the ambient temperature. Accordingly, it is advantageous to mount an indicator on the vessel for indicating the vessel temperature. Such indicators are obtainable as self-sticking strips on which microencapsulated liquid crystals are applied which show a coloring in accordance with the temperature. From temperature vapor pressure curves, the saturating vapor pressure present at the corresponding temperature can be determined and thereby also the concentration in the test substance atmosphere.

It is advantageous to provide the vessel with a thermal insulating jacket to substantially protect the vessel against temperature fluctuations. An appropriate window is provided in this jacket to make a temperature indicator visible.

An especially cost-effective embodiment of the test vessel is provided in that it consists of a styropor flask having an aluminum foil seal over the flask opening. These flasks are: inexpensive to produce, easy to transport and to store and are ideal as a one-time use articles.

It is advantageous to provide a plastic flask with an inner jacket made of aluminum in order to prevent a possible diffusion of specific vaporous substances from the flask and to render the flask resistant against such substances which could dissolve the material of which the vessel is made.

BRIEF DESCRIPTION OF THE DRAWING

The invention will now be described with reference to the single FIGURE of the drawing which shows an elevation view, in section, of a test vessel device according to an embodiment of the invention.

DESCRIPTION OF THE PREFERRED EMBODIMENTS OF THE INVENTION

The test vessel device shown in the drawing includes a flask 1 having an inner space lined with an aluminum layer 2. The flask 1 is accommodated in a cup-shaped jacket 3 for providing thermal insulation. The flask opening 4 is closed by a seal 5 in the form of an aluminum foil. The aluminum layer 2 has an upper portion which is pulled out over the edge of the flask opening and the seal 5 is welded to the inner layer 2 to form a unit. The inner side of the flask opening 4 carries a receptacle 6 in which a sensor head (not shown) of a measuring or detection device is introduced for testing. The test substance 7 is disposed on the base of the flask and is in the form of a liquid which fills the inner space of the flask 1 as a vapor. A sticker-like temperature indicator 8 is glued to the outer wall surface of the flask 1 at a suitable location. The temperature indicator can be viewed from the outside through a window 9 in the jacket 3.

It is understood that the foregoing description is that of the preferred embodiments of the invention and that various changes and modifications may be made thereto without departing from the spirit and scope of the invention as defined in the appended claims.

What is claimed is:

1. The combination of an apparatus for measuring or detecting a gas and a test vessel device for testing the apparatus, the apparatus having a sensing head and the combination comprising:
a vessel having an interior and having an upper portion defining an opening through which the sensing head of the apparatus is insertable;
a liquid disposed in said interior, said liquid being a solution composed of a solvent and a test substance of a quantity and concentration so as to cause a vapor to be present in said interior which is saturated with said test substance to provide an operationally ready test substance atmosphere for detection by the sensing head;
a penetrable seal for closing off said interior with respect to the ambient in a gastight manner until the sensing head is inserted into said opening for communicating directly with said test substance atmosphere;
said seal having a lower surface facing toward the interior of said vessel; and,
said interior of said vessel being unobstructed up to said lower surface of said seal.

2. The combination of claim 1, said test substance containing the gas to be detected by said apparatus dissolved in said solution and convertible into the vapor phase.

3. The combination of claim 1, said test substance containing a gas dissolved in said solution and convertible into the vapor phase, said gas being different from the gas to be detected by said apparatus.

4. The combination of claim 1, further comprising receiving means provided in said opening beneath said seal for receiving the sensing head in a vapor-tight manner after the sensing head has penetrated said seal.

5. A test vessel device for testing an apparatus for measuring or detecting a gas, the test vessel device comprising:
a vessel having an interior and having an upper portion defining an opening through which a sensing head of the apparatus is insertable;
a liquid disposed in said interior, said liquid being a solution composed of a solvent and a test substance of a quantity and concentration so as to cause a vapor to be present in said interior which is saturated with said test substance;
a seal penetrable by the sensing head for closing off said interior with respect to the ambient in a gas-tight manner; and,
a receptacle seated in said opening beneath said seal for accommodating the sensing head in a vapor-tight manner after the sensing head has penetrated said seal.

6. A test vessel device for testing an apparatus for measuring or detecting a gas, the test vessel device comprising:
a vessel having an interior and having an upper portion defining an opening through which a sensing head of the apparatus is insertable;
a liquid disposed in said interior, said liquid being a solution composed of a solvent and a test substance of a quantity and concentration so as to cause a vapor to be present in said interior which is saturated with said test substance;
a penetrable seal for closing off said interior with respect to the ambient in a gastight manner; and,
temperature indicating means mounted on said vessel for indicating the temperature of said vessel.

7. A test vessel device for testing an apparatus for measuring or detecting a gas, the test vessel device comprising:
a vessel having an interior and having an upper portion defining an opening through which a sensing head of the apparatus is insertable;
a liquid disposed in said interior, said liquid being a solution composed of a solvent and a test substance of a quantity and concentration so as to cause a vapor to be present in said interior which is saturated with said test substance;
a penetrable seal for closing off said interior with respect to the ambient in a gastight manner; and,
a thermally-insulating jacket encasing said vessel.

8. The test vessel device of claim 7, said jacket having a window formed therein; and, temperature indicating means mounted in said window and on said vessel for indicating the temperature of said vessel.

9. A test vessel device for testing an apparatus for measuring or detecting a gas, the test vessel device comprising:
- a vessel having an interior and having an upper portion defining an opening through which a sensing head of the apparatus is insertable;
- a liquid disposed in said interior, said liquid being a solution composed of a solvent and a test substance of a quantity and concentration so as to cause a vapor to be present in said interior which is saturated with said test substance;
- a penetrable seal for closing off said interior with respect to the ambient in a gastight manner; and,
- said vessel being a polystyrolfoam flask and said seal being an aluminum foil seal closing off said interior at said opening of said flask.

10. A test vessel device for testing an apparatus for measuring or detecting a gas, the test vessel device comprising:
- a vessel having an interior and having an upper portion defining an opening through which a sensing head of the apparatus is insertable;
- a liquid disposed in said interior, said liquid being a solution composed of a solvent and a test substance of a quantity and concentration so as to cause a vapor to be present in said interior which is saturated with said test substance;
- a penetrable seal for closing off said interior with respect to the ambient in a gastight manner; and,
- said vessel being an aluminum coated plastic flask and said seal being an aluminum foil seal closing off said interior at said opening of said flask.

11. The combination of an apparatus for measuring or detecting a gas and a test vessel device for testing the apparatus, the apparatus having a sensing head and the combination comprising:
- a vessel having an interior and having an upper portion defining an opening through which the sensing head can be introduced;
- a liquid disposed in said interior, said liquid being a solution composed of a solvent inert with respect to the sensing head and a test substance of a quantity and concentration so as to cause a vapor to be present in said interior which is saturated with said test substance;
- a penetrable seal for closing off said interior with respect to the ambient in a gastight manner;
- said seal being penetrable by the sensing head; and,
- a receptacle seated in said opening beneath said seal for accommodating the sensing head in a vapor-tight manner after the sensing head has penetrated said seal.

12. The combination of an apparatus for measuring or detecting a gas and a test vessel device for testing the apparatus, the apparatus having a sensing head and the combination comprising:
- a vessel having an interior and having an upper portion defining an opening through which the sensing head can be introduced;
- a liquid disposed in said interior, said liquid being a solution composed of a solvent inert with respect to the sensing head and a test substance of a quantity and concentration so as to cause a vapor to be present in said interior which is saturated with said test substance;
- a penetrable seal for closing off said interior with respect to the ambient in a gastight manner; and,
- temperature indicating means mounted on said vessel for indicating the temperature of said vessel.

13. The combination of an apparatus for measuring or detecting a gas and a test vessel device for testing the apparatus, the apparatus having a sensing head and the combination comprising:
- a vessel having an interior and having an upper portion defining an opening through which the sensing head can be introduced;
- a liquid disposed in said interior, said liquid being a solution composed of a solvent inert with respect to the sensing head and a test substance of a quantity and concentration so as to cause a vapor to be present in said interior which is saturated with said test substance;
- a penetrable seal for closing off said interior with respect to the ambient in a gastight manner; and,
- a thermally-insulating jacket encasing said vessel.

14. The combination of claim 13, said jacket having a window formed therein; and, temperature indicating means mounted in said window and on said vessel for indicating the temperature of said vessel.

15. The combination of an apparatus for measuring or detecting a gas and a test vessel device for testing the apparatus, the apparatus having a sensing head and the combination comprising:
- a vessel having an interior and having an upper portion defining an opening through which the sensing head can be introduced;
- a liquid disposed in said interior, said liquid being a solution composed of a solvent inert with respect to the sensing head and a test substance of a quantity and concentration so as to cause a vapor to be present in said interior which is saturated with said test substance;
- a penetrable seal for closing off said interior with respect to the ambient in a gastight manner; and,
- said vessel being a polystyrolfoam flask and said seal being an aluminum foil seal closing off said interior at said opening of said flask.

16. The combination of an apparatus for measuring or detecting a gas and a test vessel device for testing the apparatus, the apparatus having a sensing head and the combination comprising:
- a vessel having an interior and having an upper portion defining an opening through which the sensing head can be introduced;
- a liquid disposed in said interior, said liquid being a solution composed of a solvent inert with respect to the sensing head and a test substance of a quantity and concentration so as to cause a vapor to be present in said interior which is saturated with said test substance;
- a penetrable seal for closing off said interior with respect to the ambient in a gastight manner; and,
- said vessel being an aluminum coated plastic flask and said seal being an aluminum foil seal closing off said interior at said opening of said flask.

* * * * *